US012773115B2

(12) United States Patent
Loparo et al.

(10) Patent No.: US 12,773,115 B2
(45) Date of Patent: Oct. 27, 2026

(54) SYSTEMS AND METHODS FOR PREDICTING AND PREVENTING CASES OF SUDDEN UNEXPECTED INFANT DEATH CAUSED BY SUDDEN UNEXPECTED POSTNATAL COLLAPSE

(71) Applicant: Case Western Reserve University, Cleveland, OH (US)

(72) Inventors: Kenneth A. Loparo, Chesterland, OH (US); Badar J. Kayani, Columbus, OH (US); Farhad Kaffashi, Cleveland Heights, OH (US); Susan Luddington, Chagrin Falls, OH (US); Matthew McConnell, Sagamore Hills, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 344 days.

(21) Appl. No.: 18/462,001

(22) Filed: Sep. 6, 2023

(65) Prior Publication Data

US 2024/0081655 A1 Mar. 14, 2024

Related U.S. Application Data

(60) Provisional application No. 63/404,593, filed on Sep. 8, 2022.

(51) Int. Cl.
*A61B 5/0205* (2006.01)
*A61B 5/00* (2006.01)
(Continued)

(52) U.S. Cl.
CPC ............ *A61B 5/0205* (2013.01); *A61B 5/002* (2013.01); *A61B 5/14551* (2013.01);
(Continued)

(58) Field of Classification Search
CPC .................. A61B 5/0205; A61B 5/002; A61B 5/14551; A61B 5/6801; A61B 5/746;
(Continued)

(56) References Cited

U.S. PATENT DOCUMENTS 5,398,682 A * 3/1995 Lynn .................. A61B 5/14551 600/335
8,620,448 B1 * 12/2013 Delia .................. A61B 5/0095 607/62
(Continued)

*Primary Examiner* — Michael J Lau
(74) *Attorney, Agent, or Firm* — Tarolli, Sundheim, Covell & Tummino LLP

(57) ABSTRACT

A wearable device can be worn by a neonate or infant and used to monitor estimated instantaneous $SpO_2$ to prevent Sudden Unexpected Postnatal Collapse (SUPC). The wearable device includes at least one photoplethysmography sensor configured to be placed against the neonate's skin to measure pleth data and an inertial measurement unit (IMU) to collect motion data of the neonate and/or a pressure sensor. The pleth data and the motion/pressure data can be sampled for a time period. The pleth data and the motion/pressure data can be analyzed to estimate an average heartrate and compute heartrate variability features for the time period. An instantaneous $SpO_2$ can be estimated for the time period based on the pleth data, the motion data, and the heartrate variability features for the time period. The instantaneous $SpO_2$ can be characterized as healthy, watch, or dangerous; an alert can be issued when characterized as watch/dangerous.

17 Claims, 9 Drawing Sheets

(51) Int. Cl.
*A61B 5/1455* (2006.01)
*A61B 5/024* (2006.01)

(52) U.S. Cl.
CPC ............ *A61B 5/6801* (2013.01); *A61B 5/746* (2013.01); *A61B 5/02405* (2013.01); *A61B 5/02416* (2013.01); *A61B 5/02438* (2013.01); *A61B 2503/045* (2013.01); *A61B 2562/0219* (2013.01); *A61B 2562/0247* (2013.01)

(58) Field of Classification Search
CPC ........... A61B 5/02405; A61B 5/02416; A61B 5/02438; A61B 2503/045; A61B 2562/0219; A61B 2562/0247; A61B 5/1114; A61B 5/681; A61B 5/1118; A61B 5/7275; A61B 5/7282
See application file for complete search history.

(56) References Cited

U.S. PATENT DOCUMENTS

| | | | | |
|---|---|---|---|---|
| 9,195,799 | B2 | 11/2015 | Sze et al. | |
| 9,775,529 | B2 | 10/2017 | Moon et al. | |
| 9,955,877 | B2 | 5/2018 | Delia | |
| 10,297,143 | B1 * | 5/2019 | Giffen | A61B 5/0205 |
| 10,646,144 | B2 | 5/2020 | Lamego | |
| 11,172,890 | B2 | 11/2021 | Al-Ali et al. | |
| 11,331,016 | B1 * | 5/2022 | Mohammadi | A61B 5/14552 |
| 2010/0168528 | A1 * | 7/2010 | Evans | A61B 5/02405 600/301 |
| 2010/0179389 | A1 * | 7/2010 | Moroney, III | A61B 5/6819 119/857 |
| 2010/0298728 | A1 * | 11/2010 | Addison | A61B 5/726 600/504 |
| 2012/0150002 | A1 * | 6/2012 | Shelley | G01N 33/497 600/323 |
| 2016/0262637 | A1 * | 9/2016 | Delia | A61B 5/02055 |
| 2017/0164850 | A1 * | 6/2017 | Murphy | A61B 5/742 |
| 2018/0070886 | A1 * | 3/2018 | Fairchild | A61B 5/48 |
| 2018/0146870 | A1 * | 5/2018 | Shemesh | A61B 5/02416 |
| 2019/0090820 | A1 * | 3/2019 | Schwenk | A61B 5/721 |
| 2019/0380901 | A1 * | 12/2019 | Breegi | A61G 13/108 |
| 2020/0253547 | A1 * | 8/2020 | Harris | A61B 5/7203 |
| 2020/0281526 | A1 * | 9/2020 | Carpenter | A61B 5/6803 |
| 2020/0375513 | A1 * | 12/2020 | Kasbekar | A61B 5/14552 |
| 2021/0022676 | A1 * | 1/2021 | Lamego | A61B 5/0002 |
| 2021/0251571 | A1 * | 8/2021 | Morgan | D04B 1/16 |
| 2021/0386300 | A1 * | 12/2021 | Rogers | A61B 5/0006 |

* cited by examiner

SYSTEMS AND METHODS FOR PREDICTING AND PREVENTING CASES OF SUDDEN UNEXPECTED INFANT DEATH CAUSED BY SUDDEN UNEXPECTED POSTNATAL COLLAPSE

CROSS-REFERENCE TO RELATED APPLICATIONS

This application claims the benefit of U.S. Provisional Application Ser. No. 63/404,593, filed 8 Sep. 2022, entitled "SYSTEMS AND METHODS FOR PREVENTING SUDDEN UNEXPECTED POSTNATAL COLLAPSE". The entirety of this application is incorporated by reference for all purposes.

TECHNICAL FIELD

This disclosure relates generally to predicting and preventing cases of sudden unexpected infant death (SUID) caused by sudden unexpected postnatal collapse (SUPC) and more specifically to systems and methods that use a wireless and wearable device to provide an estimate of instantaneous oxygen saturation ($SpO_2$) in a neonate (or other infant) by monitoring the neonate (or other infant) to predict and prevent SUPC.

BACKGROUND

Infant mortality, the death of young children under the age of one, is a distressing problem that can have many tragic causes. One important cause of infant mortality is Sudden Unexpected Infant Death (SUID) caused by sudden unexpected postnatal collapse (SUPC). The onset of SUPC, which generally affects apparently healthy neonates and/or infants (e.g., neonates less than four weeks old or infants less than one year old), may be due to airway occlusion without clear warning or cause. SUPC can lead to death or lifelong disability due to the neonate's or infant's body receiving a lack of oxygen for a time. For example, the air way occlusion can occur after breast feeding (either in the hospital or at home) due to limited support of the head and neck or the infant's face may become embedded in the mother's breast tissue. In many cases, if discovered quickly, the airway occlusion may be cleared and SUPC prevented. Such prevention requires continuous monitoring of the neonate's $SpO_2$ over time to detect changes that can predict and/or indicate a problem and then quick action to correct the lack of oxygen. However, the $SpO_2$ of normal term, generally healthy infants, is not routinely monitored over time (e.g., with pulse oximetry), in the hospital or at home for reasons including cost, inconvenience, interruption of maternal-infant bonding, and hinderance of breastfeeding.

SUMMARY

Described herein are systems and methods that use a wireless and wearable device (referred to herein as a "wearable device") to provide an estimate of instantaneous oxygen saturation ($SpO_2$) in a neonate (or other infant) by monitoring the instantaneous $SpO_2$ to predict and prevent Sudden Unexpected Postnatal Collapse (SUPC) (and other causes of Sudden Infant Death).

In an aspect, the present disclosure can include a wearable device configured to be worn by a neonate (or other infant). The wearable device includes at least one photoplethysmography sensor configured to be placed against the neonate's skin and to measure and collect plethysmography (pleth) data; an inertial measurement unit (IMU) configured to collect motion data of the neonate; and, in some instances, a pressure sensor to monitor the contact pressure between the at least one photoplethysmography sensor and the neonate's skin. The at least one photoplethysmography sensor, the pressure sensor, and the IMU are in communication with a processor that: samples the pleth data for a time period and the motion data for the time period; in some instances, determines the quality of the pleth data; analyzes the pleth data and the motion data for the time period to estimate an average heartrate and compute at least one heartrate variability features for the time period; estimates an instantaneous $SpO_2$ for the time period based on the pleth data for the time period, the motion data for the time period, and the at least one heartrate variability features for the time period; characterizes the instantaneous $SpO_2$ as healthy, watch, or dangerous; and issues an alert when the instantaneous $SpO_2$ is characterized as watch or dangerous.

In another aspect, the present disclosure can include a system that can be used to prevent SU PC. The system includes a wearable device configured to be worn by a neonate (or other infant). The wearable device includes at least one photoplethysmography sensor configured to be placed against the neonate's skin and to measure and collect pleth data; (in some instances) a pressure sensor to monitor the contact pressure between the at least one photoplethysmography sensor and the neonate's skin; and an inertial measurement unit (IMU) configured to collect motion data of the neonate. The pressure sensor, the at least one photoplethysmography sensor, and the IMU are in communication with a processor that: samples the pleth data for a time period and the motion data for the time period; in some instances, determines the quality of the pleth data; analyzes the pleth data and the motion data for the time period to estimate an average heartrate and compute at least one heartrate variability features for the time period; estimates an instantaneous $SpO_2$ for the time period based on the pleth data for the time period, the motion data for the time period, and the at least one heartrate variability features for the time period; characterizes the instantaneous $SpO_2$ as healthy, watch, or dangerous; and issues an alert when the instantaneous $SpO_2$ is characterized as watch or dangerous. The system also includes one or more devices that can be held by a caregiver so that the caregiver can receive the alert and take preventative action to prevent SUPC events.

In a further aspect, the present disclosure can include a method for preventing SUPC. The method can be executed by a system comprising a processor and includes: receiving at least one signal comprising pleth data from at least one photoplethysmography sensor of a wearable device and a signal comprising motion data signal from an inertial measurement unit (IMU) of the wearable device; sampling the pleth data and the motion data for the time period; analyzing the pleth data for the time period and the motion data for the time period to estimate an average heartrate and at least one heartrate variability features for the time period; estimating an instantaneous $SpO_2$ of the neonate wearing the wearable device for the time period based on the pleth data for the time period and the at least one heartrate variability features for the time period; and characterizing the instantaneous $SpO_2$ for the time period as healthy, watch, or dangerous. An alarm is issued when the instantaneous $SpO_2$ is characterized as watch or dangerous indicating an enhanced risk of SUPC.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
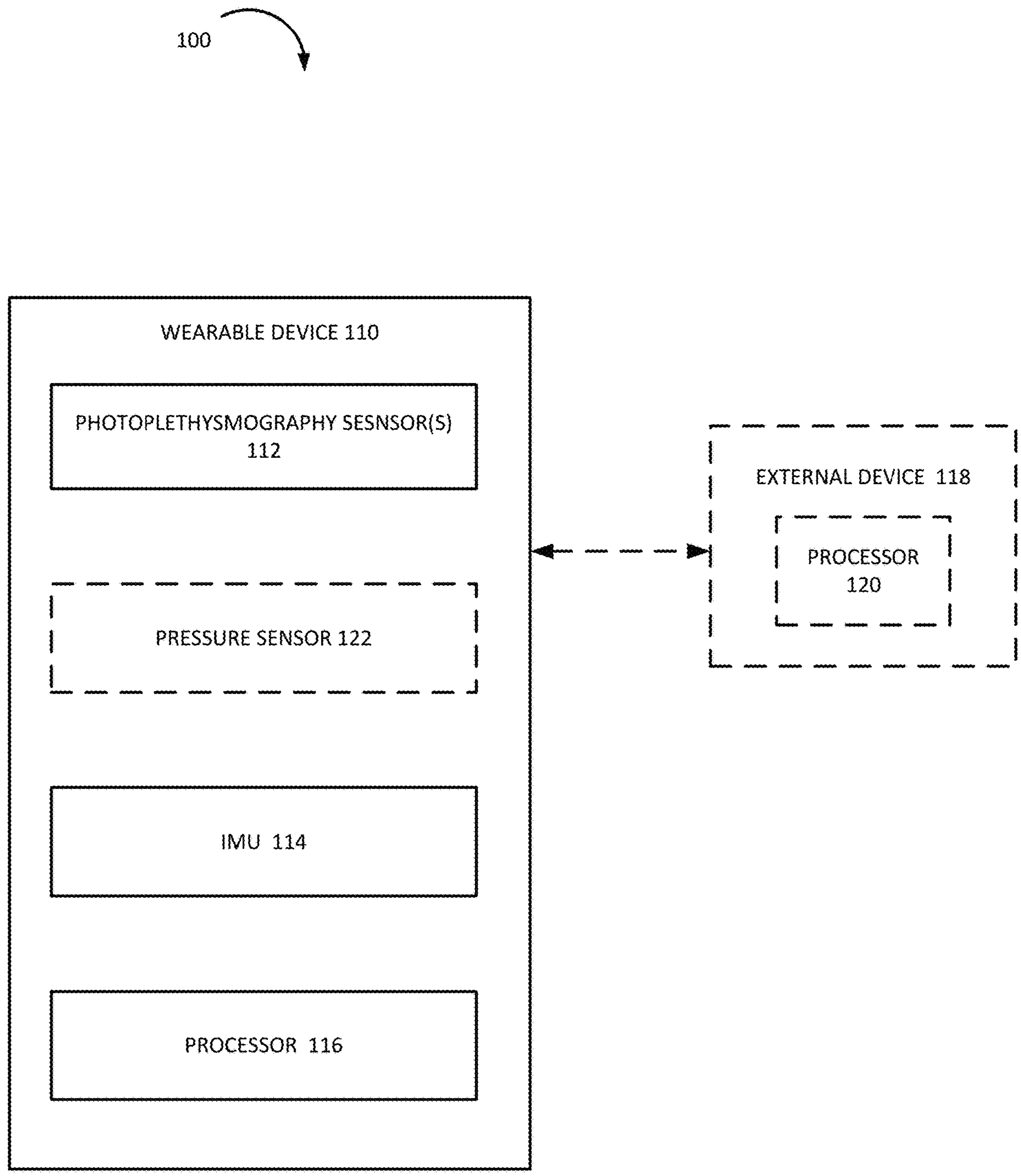
FIG. 1 is a block diagram showing an example system that can monitor $SpO_2$ in a neonate (or other infant)

Unless otherwise defined, all technical terms used herein have the same meaning as commonly understood by one of ordinary skill in the art to which the present disclosure pertains.

As used herein, the singular forms "a," "an," and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "Sudden Unexpected Infant Death", also referred to as "SUID", can refer to the sudden and unexpected death of a baby less than one year old in which the cause was not obvious before investigation. In other words, SUID includes all unexpected deaths without a clear cause and those deaths from a known cause that can be determined after death.

As used herein, the term "Sudden Unexpected Postnatal Collapse", also referred to as "SUPC", can refer to a type of SUID that involves the sudden collapse of an apparently healthy neonate or infant. A SUPC diagnosis is restricted to a neonate or infant who is regarded as healthy at birth and deemed well enough to receive routine postnatal care (as opposed to enhanced postnatal care) but then collapses unexpectedly (e.g., is discovered in a state of cardiorespiratory extremis) and either dies or goes on to require intensive care.

As used herein, the term "infant" can refer to a baby less than one year old.

As used herein, the terms "neonate" or "newborn" can refer to an infant who is less than four weeks old.

As used herein, the term "caregiver" can refer to any person responsible for an infant or neonate's health and wellbeing. The caregiver can be a parent, a sibling, a grandparent, a relative, a medical professional, or the like.

As used herein, the term "photoplethysmography", or "PPG", can refer to an optical technique that can detect volumetric changes in blood in peripheral circulation (e.g., in the microvascular bed of tissue).

As used herein, the term "photoplethysmography device" (e.g., a pulse oximeter) can refer to a system that can illuminate a portion of a patient's skin and measure changes in light absorption through the cardiac cycle by measuring the amount of light transmitted through or reflected by a blood volume through the skin. The photoplethysmography device can include one or more light sources and a sensor configured to detect pleth data reflective of the volumetric changes of blood.

As used herein, the term "pleth data" can refer to the data obtained from a photoplethysmography sensor related to blood volume changes in the microvascular bed of tissue. For example, the pleth data can be represented as a variable waveform (e.g., sinusoidal-like variability) with varying amplitudes per phase. The pleth data can have an AC component and/or a DC component each corresponding to at least one variable cardiorespiratory response (e.g., blood volume, heartbeat, respiration rate, or the like). For example, the DC component may be attributable to the bulk absorption of the skin tissue, while the AC component may be attributable to variation in blood volume in the skin caused by the pulse pressure of the cardiac signal (so that the height of the AC component is proportional to the pulse pressure).

As used herein, the term "inertial measurement unit", also referred to as "IMU", can refer to a device or portion of the device that can measure and report data related to an object (or person) to which the IMU is attached, including motion measurements such as linear and angular accelerations, linear and angular velocities, orientation, and the like. For example, an IMU can include at least one of one or more gyroscopes (e.g., for providing a measure of angular rate), one or more accelerometers (e.g., for providing a measure of specific force/acceleration), and one or more magnetometers (e.g., for measuring magnetic fields and/or magnetic dipole moments).

As used herein, the term "heartrate" can refer to the number of times a heart beats within a time period (generally one minute).

As used herein, the term "heartrate variability" can refer to fluctuations in the time intervals between adjacent heartbeats.

As used herein, the term "heartrate variability features" can refer to metrics of heartrate variability, that can be quantified in the time-domain or the frequency-domain.

As used herein, the term "$SpO_2$", also known as "oxygen saturation" or "peripheral oxygen saturation", can refer to a measure of the amount of oxygen-carrying hemoglobin in blood relative to the total amount of hemoglobin (e.g., oxygen-carrying hemoglobin plus hemoglobin not carrying oxygen). Generally, $SpO_2$ is measured with pulse oximetry and is considered an estimate of the true arterial oxygen saturation of a patient. True arterial oxygen saturate ($SaO_2$) can be measured at a time with a blood gas analysis test, however such tests can only be done for a time blood is drawn, take time to get results, and are invasive. As such, $SpO_2$ can also be referred to herein as "instantaneous $SpO_2$" or "estimated instantaneous $SpO_2$".

As used herein, the term "medical procedure" can refer to a therapeutic treatment action, for example, delivery of supplemental oxygen, shifting the infant or the neonate to a different physical position, or the like.

As used herein, the term "wearable" when used to modify terms like device, sensor, and the like, can refer a device that is wireless and configured to be worn on/by/against/near a portion of a body for collection of substantially real-time physiological signals and analysis of the available data to provide clinically meaningful parameters related to health status. The wearable device can be sized and dimensioned to by worn by a neonate or other infant, in some instances, to provide the meaningful parameters related to the health status of the neonate or other infant.

II. Overview

Infant mortality is an unmet clinical need that has a significant impact on humanity through population health and Sudden Unexpected Infant Deaths (SUIDs) is an important contributor. The prevalence of SUID, which includes all unexpected deaths without a clear cause, has increased in recent years. Sudden unexpected postnatal collapse (SUPC) is one rare subset of SUID that affects apparently healthy neonates/infants (e.g., neonates less than four weeks old and infants less than one year old) and can be fatal in approximately half of cases and cause long term disabilities in survivors. Such unexplained deaths, and preventable disabilities, are a shocking tragedy, often found later to be due to unexpected airway occlusion that could have been prevented by frequent monitoring of the neonate's/infant's blood oxygen saturation ($SpO_2$) to detect small changes and fast action to remedy the lack of oxygen. Unfortunately, due to cost and personal restraints, as well as equipment-based problems and inaccuracies in children so young, such monitoring is generally not done for normal term, generally healthy infants. In fact, detecting changes in the infant's heartrate, motion, and blood oxygen saturation can be preventive measures, but normal term infants are not currently monitored directly after birth due to cost, and because of the hardware and cumbersome wires that are required when using standard monitoring systems—all of which are believed to interrupt maternal-infant bonding and hinder breastfeeding. Obstetric nurses, generally, know very little about signs of SUPC and are not watching newborn behaviors constantly. The unmet need is to accurately monitor healthy infants in clinical and home settings to prevent neonate/infant deaths from SUPC, as well as infant deaths from SUID generally. It has been discovered that measuring instantaneous $SpO_2$ can provide insight into the small changes which can indicate a risk for SUPC or more widely for SUID.

An inexpensive wearable device can be used to predict and prevent SUPC (and more generally SUID) non-invasively. The inexpensive wearable device can be configured to be worn on skin of an infant of any age, such as a neonate, and can include sensors that can be used to estimate instantaneous $SpO_2$ and warn of potentially dangerous decreases in oxygen saturation levels. For example, the sensors can include at least one photoplethysmography sensor that can be placed against the neonate's skin to measure pleth data, an inertial measurement unit (IMU) that can collect motion data, and a pressure sensor that can monitor contact pressure between the at least one photoplethysmography sensor and the neonate's skin (a similar device can be constructed to be used by an infant). The pleth data, the motion data and the pressure data for the time period can be sampled. The sampled data can be analyzed to estimate an average heartrate and compute at least one heartrate variability features for the time period. The instantaneous $SpO_2$ for the time period can be determined based on the pleth data for the time period, the motion data for the time period, and the at least one heartrate variability features for the time period, and the instantaneous $SpO_2$ can be categorized as healthy, watch, or dangerous. An alert can be issued when the contact pressure drops below a predetermined value or when the instantaneous $SpO_2$ is characterized as watch or dangerous. Accordingly, the wearable device can be an inexpensive way to prevent SU PC.

III. Systems

An aspect of the present disclosure relates to a system 100 (FIG. 1) that includes a wearable device 110, which may be embodied in a small package, to monitor an estimated $SpO_2$ in a neonate (or other infant) instantaneously (e.g., within 1 second, five seconds, 10 seconds, or the like). It should be understood that, although described as being sized and dimensioned for a neonate, the system 100 can be sized and dimensioned for any infant less than 12 months old. Being able to take estimates of instantaneous $SpO_2$ non-invasively is an advantage over traditional invasive and expensive methods of monitoring (and even predicting) $SpO_2$ in a neonate (or other infant). The $SpO_2$ can be monitored, and predicted, by the system 100, in order to predict and prevent Sudden Unexpected Postnatal Collapse (SUPC) (or SUID more generally). As described herein, the system 100 is designed to work with neonates specifically, but it should be understood that the system 100 can work with infants of any age (e.g., any baby under the age of one year) with minimal modifications (e.g., changing the size of one or more components of the system 100, changing one or more programmed criteria and/or thresholds, or the like). As shown in FIG. 1, the system 100 can include a wearable device 110 that may be in communication (e.g., wired and/or wireless) with one or more external devices (represented as external device 118) that may be associated with one or more caregivers of a neonate (or infant). The system 100 can, for instance, be used to track and predict estimated $SpO_2$ and alert if $SpO_2$ falls or trends towards falling below a certain level, while self-identifying motion and/or pressure related problems with data quality.

The wearable device 110 can include at least one photoplethysmography sensor (photoplethysmography sensor(s) 112) that can be placed against the skin of a neonate wearing the wearable device 110 and can measure pleth data. The at least one photoplethysmography sensor can include one or more light sources, as well as one or more detectors. The one or more light sources can include an infrared (IR) light source, a red light source, a blue light source, and/or a green light source. The one or more light sources can be, for example, one or more LEDs. In certain instances, the photoplethysmography sensor can include two or more LEDs, three or more LEDs, four or more LEDs, or the like. In one instance, the photoplethysmography sensor(s) 112 can include an IR LED, a red LED, a blue LED, and a green LED configured to direct light towards the skin of the neonate wearing the wearable device. The one or more detectors of the at least one photoplethysmography sensor can detect the transmission of light through the skin of the neonate and/or the reflectance of light off the skin of the neonate to measure pleth data. The one or more detectors can be, for example, one or more photodetectors. The photoplethysmography sensor(s) 112 can convert the measurements of the one or more detectors into raw pleth waveforms (e.g., pleth data). The wearable device 110 can also include an Inertial measurement unit (IMU) 114 that can collect motion data of the neonate. As an example, the motion data can include position data, velocity data, orientation data, inertia data, acceleration data, or the like. The wearable device 110 can also include a pressure sensor 122 (shown as a box with dashed lines to show the optional nature) that can detect and/or determine the contact pressure of the wearable device 110 on the skin of the neonate wearing the wearable device. Additionally, while not shown, the wearable device can also include one or more alert mechanisms for audio, visual, and/or haptic alerts (e.g., speaker, LEDs, haptic motor, or the like).

The wearable device 110 can further include processor 116 that can be in communication with the IMU 114, the photoplethysmography sensor(s) 112, and the pressure sensor 122. Additionally, the wearable device 110, including at least one of the IMU 114, the photoplethysmography sensor(s) 112, the pressure sensor 122, and the processor 116, may also be in communication with a processor 120 of external device 118. The external device 118 can be, for example, a caregiver's and/or health professional's base station, a mobile phone, a computer, or the like, which may also include a display and/or a user interface. In some instances, the caregiver can be at the same location as the neonate (so the communication only needs a short-range wireless communication ability, like BLUETOOTH®). In other instances, the caregiver and/or health professional may be at a remote location from the neonate (so the communication needs a long-range wireless communication ability, like WiFi). Processor 116 and processor 120 can be in communication with one or more non-transitory memories that can store instructions to be executed by either or a combination of the processors. The processor 116 and/or the processor 120 can include the non-transitory memory in some instances. In some instances, the processor 116 and/or the processor 120 can be embodied, as an example, as one or more microprocessors.

The wearable device 110 and/or the external device 118 can include at least a wireless transmitter and in some instances a wireless receiver and/or wireless transceiver (not shown). The processor 116 and/or the processor 120 can at least partially wirelessly communicate between at least one of the wearable devices 110, the external device 118, and other external devices such as one or more medical devices to enable medical treatment when the neonate has an $SpO_2$ that is below a certain characterization threshold, or the like. Communication between the wearable device 110 and external device 118 can be wireless, wired, or a combination of wired and wireless connection. For example, the wearable device 110 can include a wireless communication mechanism, wherein the wireless communication mechanism is configured to transmit the pleth data and the motion data to a base station according to a wireless communication protocol. The wireless communication protocol can be BLUETOOTH®, BLUETOOTH® low energy, WiFi, or the like.

Generally, as a non-limiting example, the wearable device 110 can be a small device configured to be worn on a body part, e.g., a foot of a neonate or other infant and used as follows. The wearable device 110 can include a means for attachment to an extremity of the neonate. The wearable device is capable of self-power (e.g., via one or more batteries, which can be replaceable or rechargeable) and wireless operation (e.g., via Bluetooth, or the like) allowing continuous (e.g., 24/7) monitoring in a clinical and/or home setting.

Figure 5:
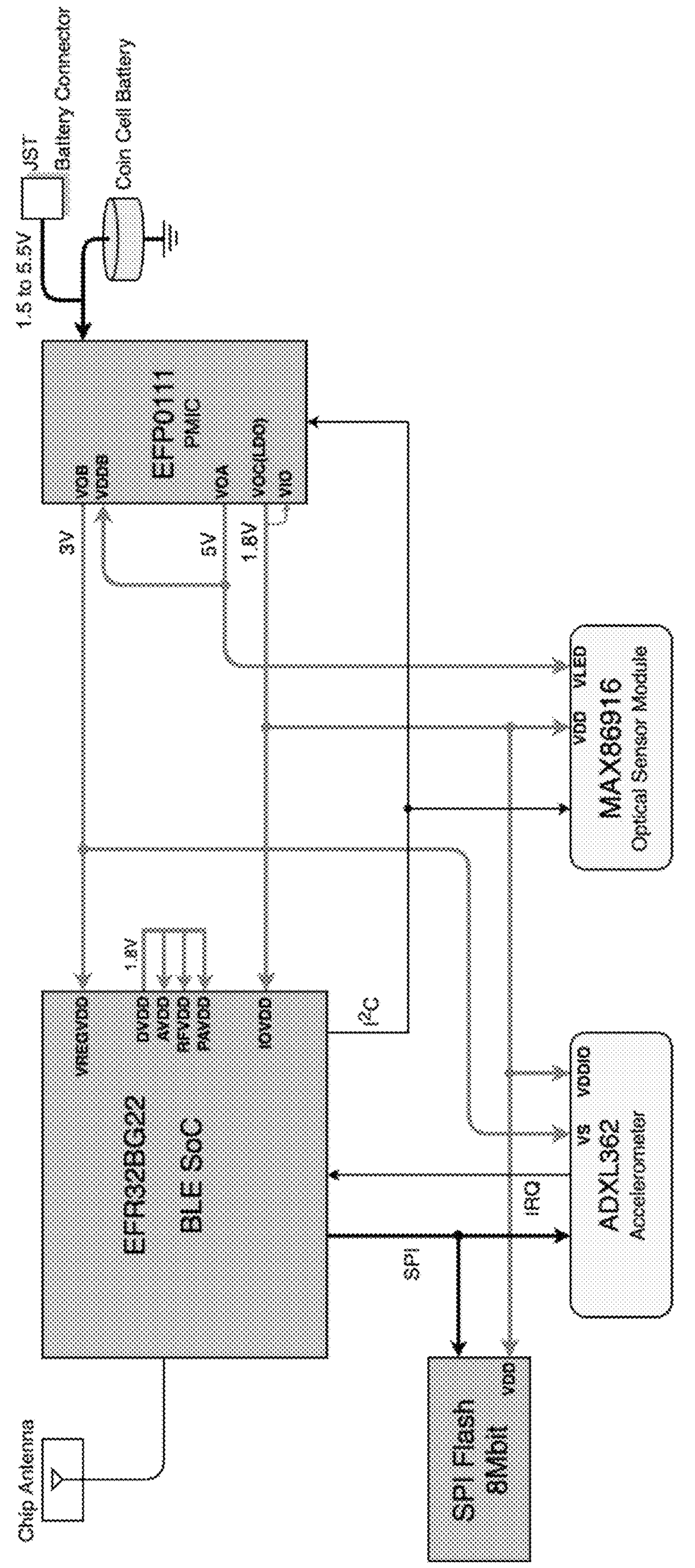
FIG. 5 shows a schematic of the circuitry required by the example of the wearable device of FIG. 1.

The wearable device 110 can include sensors to collect at least motion data, pressure data, and pleth waveform data (example configuration shown in FIG. 5). The sensor that collects at least motion data can be at least one inertial measurement unit 114, which can continuously detect motion data such as linear and angular accelerations, linear and angular velocities, orientation, and the like. The sensor that collects pressure data can include at least one pressure sensor 122 positioned on/in the wearable device 110 to detect if the sensor is in contact with the skin, ensuring accurate readings and assisting novice caregivers how to attach the wearable device for the most accurate results (e.g., highest quality pleth waveforms). The at least one plethysmography sensor 112 can have LEDs that can provide infrared, at least one of red, green, and blue wavelengths of light to the skin of the neonate (or older infant) and at least one detector that can receive reflected light from the skin. Pleth waveforms can be based on the reflected light.

The wearable device 110 can wirelessly communicate with an external device 118 (e.g., a smart phone, tablet, custom device interface, computer, or the like) at regular intervals for continuous monitoring. The wearable device 110 can additionally include all necessary hardware and/or software for at least processing the raw data provided by the sensors (e.g., processor 116). Data processing (computations) can be done by the wearable device (e.g., processor 116) and/or by the external device (e.g., processor 120). If done by the external device 118, raw sensor data can be transmitted on regular intervals from the wearable device 110 to the external device for computations, sending alarms, data visualization, data analysis, and data archiving. If done by the wearable device 110 itself, raw data and estimates can be routinely transmitted to the external device 118 for data visualization, data analysis, and data archiving (see, e.g., FIG. 2). The wearable device 110 can also include one or more speakers for audible alarms and/or LEDs for visual alarms (e.g., three LEDS—Green for safe, Yellow for caution, and Red for unsafe) that are not shown in FIG. 1.

In addition to the sensors, the wearable device 110 can also include hardware (not shown) that enables wireless communication (e.g., via the Bluetooth protocol) and electronics and circuitry required to drive the sensors/continuously collect data from the sensors. Wireless communication can be used at least to send data from the wearable device 110 to one or more external devices 118 (e.g., a phone, a tablet, a custom interface device, or the like) and store data (e.g., raw data from the sensors, the continuous $SpO_2$, and HR/PR estimates). Computations can be done by the wearable device 110 and/or by the one or more external devices 118 (selected by a user). Based on the computations, the wearable device 110 can alert (e.g., via an audio alarm and/or a visual signal) one or more users of the neonate's $SpO_2$ condition. The alert and/or warning can be programmed to indicate when the neonate is in, or is trending towards, the cautionary or unsafe range of $SpO_2$.

Figure 2:
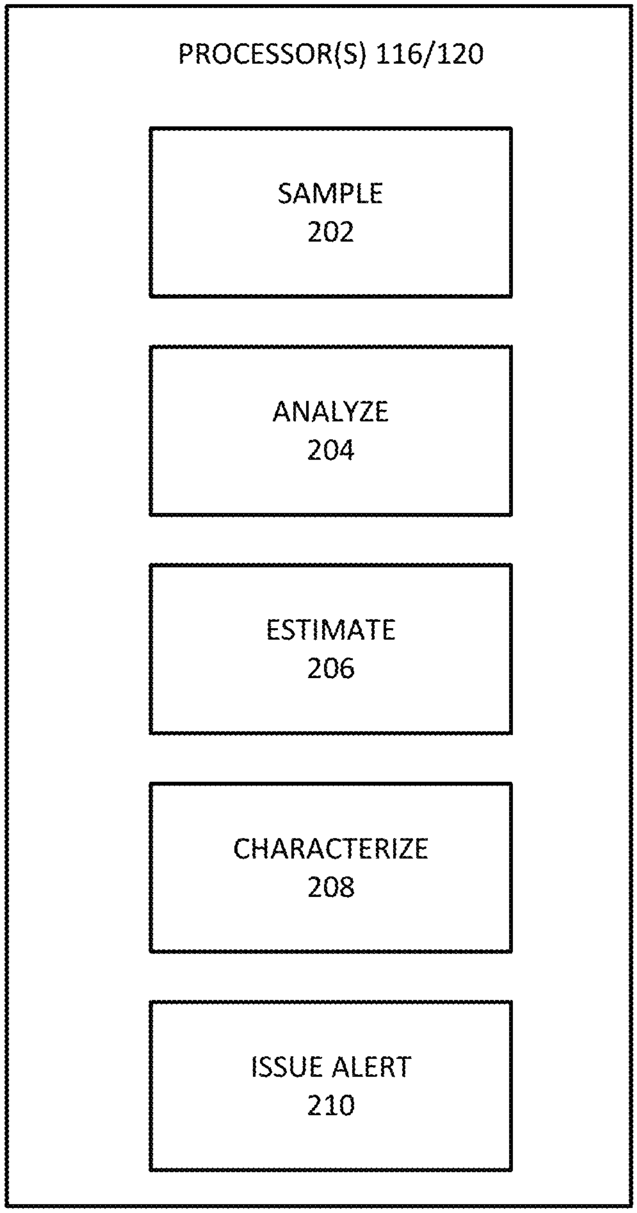
FIG. 2 is a block diagram showing the commands at least one of the processors of FIG. 1 (in the wearable device and/or external device) can execute.

FIG. 2 shows commands that can be executed partially or fully by processor 116 of the wearable device 110 and/or partially or fully by processor 120 of external device 118. The processors 116 and/or 120 can sample 202 the pleth data for a time period and the motion data for the same time period. The time period can be, for example, 10 seconds, 30 seconds, 1 minute, 2 minutes, or the like. The time period can be pre-programmed and may be changeable. The motion data can be sent to the processor 116 and/or the processor 120 from the IMU 114 and can relate to the motion of the neonate. For example, the motion data can include information about if the neonate sleeping, if the neonate is held in a sitting position, if the neonate moving (e.g., if the wearable device is worn on a foot of the neonate, is the neonate moving the foot), or the like. The pleth data can be raw pleth waveforms sent from the photoplethysmography sensor(s) 112 to the processor 116 and/or 120. The pleth waveform(s) can be determined by the photoplethysmography sensor(s) 112 based on the measurements taken by the one or more detectors in response to the one or more light sources being shone at the skin of the neonate.

The morphology of the pleth waveform depends on the amount of light that is absorbed or reflected between an LED emitter (e.g., light source), the skin (including all layers, fat, and blood in veins in the skin), and a photo detector. The raw pleth waveform includes a nonpulsatile (DC) component and a pulsatile (AC) component. The nonpulsatile (DC) component is inversely proportional to light absorption and scattering by nonpulsatile tissues at the location where the sensor is attached, including nonpulsatile blood (arterial and venous). The pulsatile (AC) component is oscillating at the pulse frequency and is representative of the blood in the arterial side of the circulation. The pleth waveforms from the wearable device 110 are thus tracking changes in blood volume within a vicinity of where the sensor is attached. The larger the blood volume (vasodilation), the more light is being absorbed, so the reflected light measured by the photo detector is smaller. Thus, the pleth waveform oscillates with the cardiac cycle and the amount of light reflected during systole through the finger, foot, or other suitable appendage, is less than during diastole.

Hemoglobin (Hb) exhibits positive cooperativity, i.e., if an $O_2$ molecule binds to one of the four hemoglobin binding sites, the affinity to oxygen of the three remaining available binding sites increases, other $O_2$ molecules are more likely to bind to the hemoglobin that is bound to one $O_2$ molecule as to another hemoglobin where no $O_2$ molecules are bound. Thus, the oxygen dissociation curve allows for more rapid loading of oxygen molecules in oxygen rich environments and easier offloading in oxygen-deficient environments. The deoxygenated form of hemoglobin with low affinity for $O_2$ promotes the release/unloading of $O_2$, and the oxygenated form of hemoglobin with high affinity for $O_2$ promotes oxygen loading. The two different configurations of hemoglobin (oxygenated and deoxygenated) have different light emitting properties that are also dependent on the specific wavelength of the light. Estimating $SpO_2$ from the pleth waveform takes advantage of these light absorption and reflection properties of hemoglobin. For example, the light absorption and reflection properties for IR light (e.g., around about 940 nm wavelength) and Red light (e.g., around about 660 nm wavelength) differ significantly between oxygenated and deoxygenated hemoglobin.

The processors 116 and/or 120 can analyze 204 the pleth data for the time period and the motion data for the time period to estimate an average heartrate and to compute at least one heartrate variability features for the time period. The analysis 204 can include extracting at least one time-domain pleth feature and/or extracting at least one frequency-domain pleth feature from the pleth data for the time period. The pleth data can be converted from time-domain to frequency-domain (or vice versa) via, for example, a Fourier Transform, a Z Transform, a Laplace Transform, or the like. The motion data can be analyzed 204 to determine, for example, at least one of position, velocity, acceleration, and orientation of the limb wearing the wearable device 110. The processors 116 and/or 120 can estimate 206 the instantaneous $SpO_2$ for the time period based on the pleth data for the time period, the motion data for the time period, and the at least one heartrate variability features for the time period. The estimation 206 of the instantaneous $SpO_2$ value for the time period can further be based on the at least one heartrate variability features for the time period and the at least one time-domain pleth feature and/or the at least one frequency-domain pleth feature extracted during the analysis 204. The processors 116 and/or 120 can characterize 208 the instantaneous $SpO_2$ as healthy, watch or dangerous. The thresholds of the characterizations can be standard and/or defined for a specific neonate (within safety bounds set for the specific neonate).

As an example, the estimate of $SpO_2$ at the time can be determined by analyzing features extracted from the pleth waveform (e.g., heart rate/pulse rare (HR/PR), non-pulsatile (DC) and pulsatile (AC) components of blood flow, and measures of pulse rate (PR) variability). The accuracy of the $SpO_2$ estimates can be conditioned on the analysis of raw motion data from the IMU and raw pressure data from the pressure sensor that ensure the sensor maintains good contact with the sole of the foot. If either predetermined motion and pressure criteria for good signal quality are not satisfied, the $SpO_2$ estimate is not updated from the previous value, the sliding window is incremented, and the new data is analyzed. Additionally, if motion and pressure criteria are not met for a predetermined amount of time, then alerts can be generated to indicate lack of motion, too much motion, and improper contact pressure between the wearable device and the neonate's skin. A new estimate of instantaneous $SpO_2$ can be obtained every 1-second and compared against previous estimates. A sliding window approach allows reevaluation of the estimates of $SpO_2$ every one minute. Predictions of future values of $SpO_2$ estimates can be determined using at least an analysis of HR/PR variability compared to clinically predetermined thresholds to predict if oxygen saturation is moving towards a cautionary or unsafe range.

The characterizations can be based on patient specific thresholds or on population-based thresholds of healthy, trending down, and unhealthy instantaneous $SpO_2$. For example, a healthy characterization can be given when the instantaneous $SpO_2$ is 95 or above, a watch characterization can be given when the instantaneous $SpO_2$ is between 94 and 89, a dangerous characterization can be given when the instantaneous $SpO_2$ is 88 or below. In another example, a healthy characterization can be given when the instantaneous $SpO_2$ is 92 or above, and an unsafe characterization can be given when the instantaneous $SpO_2$ is lower than 92. Additionally, the characterization thresholds can be any other values considered medically relevant based on population data or can be set by a health professional and/or caregiver (within predetermined safety limits that have been set to specific limits for the neonate or other infant being monitored) according to personalized patient data. When the instantaneous $SpO_2$ is characterized as watch unsafe, or dangerous, then the processors 116 and/or 120 can issue an alert 210. The alert can be audible, tactile, and/or visual. The alert can be, for example, an audible alarm from the wearable device 110 or the external device 118 that may also include a visual notification of the characterization and the estimated instantaneous $SpO_2$, the visual notification may also include a visual or previous estimated instantaneous $SpO_2$ for a plurality of preceding time periods to show a visual trend. In one example, the wearable device can include a red LED, a yellow LED, and a green LED, and the light change according to the alert status (e.g., green is healthy, yellow is watch, and red is unsafe/dangerous).

The processor 116 and/or the processor 120 can also be in communication with at least one medical device and can trigger the at least one medical device to perform a medical procedure on the neonate wearing the wearable device 110 when the instantaneous $SpO_2$ is characterized as watch or dangerous. For example, the medical device can be a tactile stimulator that uses light mechanical stimulation to activate cutaneous mechanoreceptors to activate nerve signals beneath the skin's surface and the medical procedure can be the delivery of tactile stimulation to the neonate. In another example, the medical device can be a device that can provide supplementary oxygen to the neonate and the medical procedure can be the delivery of supplemental oxygen to the neonate.

Figure 3:
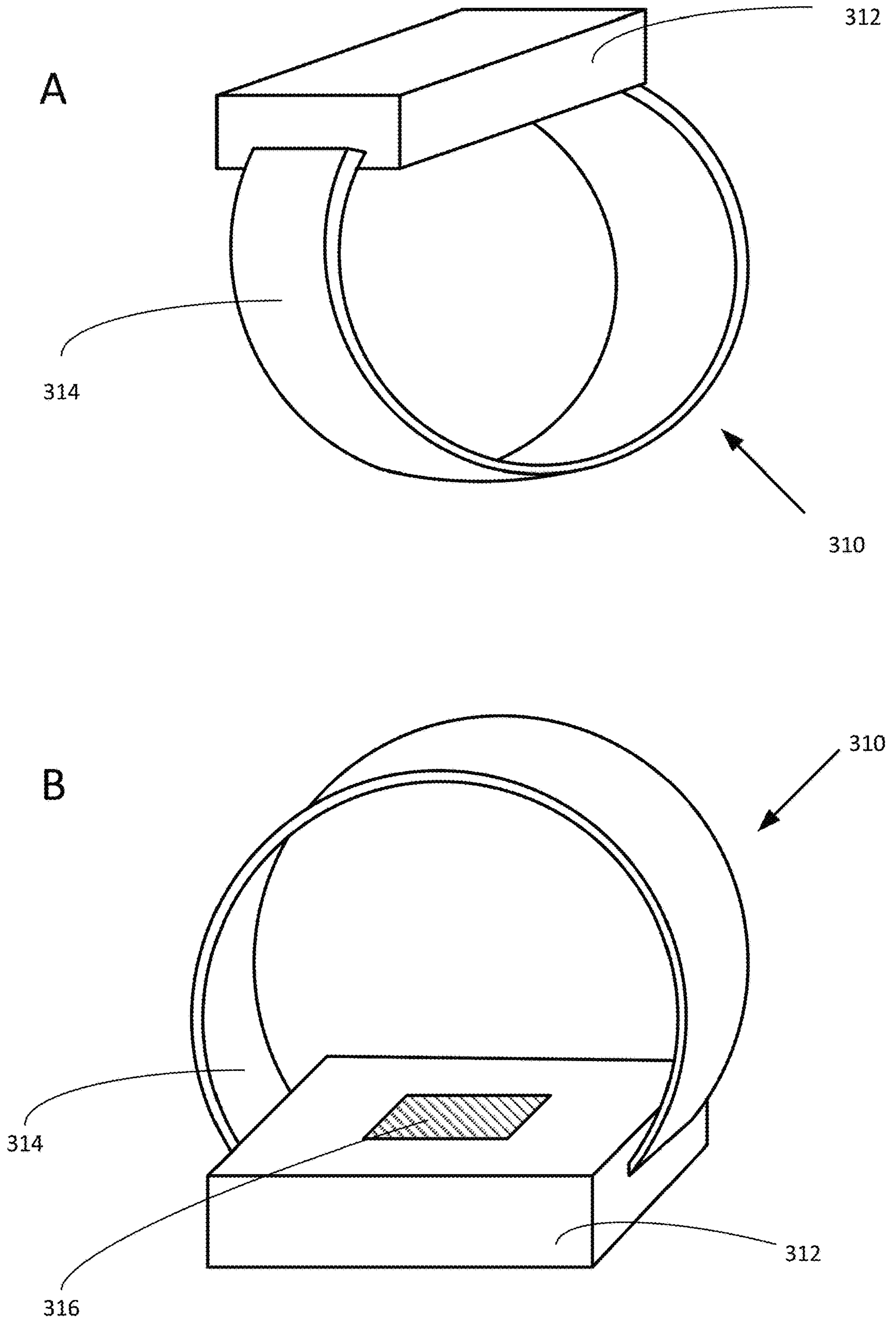
FIG. 3 shows example illustrations of two views of an example wearable device of FIG. 1.

FIG. 3 shows an exemplary wearable device 310 in two different side views in element A (right side up) and element B (upside down). The wearable device 310 can be, for example, fit to the foot of a neonate. However, the wearable device 310 can be configured to fit on and/or against any part of the neonate's body (e.g., a wrist, an arm, a leg, a stomach, etc.). The wearable device can be adjustable to fit on neonates of various sizes and/or any infant under the age of 1 but may also fit older children with only small adjustments.

The wearable device 310 can include a housing 312 that can at least partially enclose the sensor unit 316. The sensor unit 316 can include the at least one photoplethysmography sensor, the IMU, and the pressure sensor. The wearable device 310 can also include a power source (not shown), any circuitry required to drive the sensors in the sensor unit 316 and/or continuously collect data from the sensors, and a wireless communication mechanism (not shown) fully enclosed in the housing 312. The power source can be a one or more rechargeable or replaceable batteries to provide self-power and allow continuous (e.g., 24/7) monitoring in a clinical and/or a home setting. Wireless communication can be used at least to send data from the wearable device to one or more external devices (e.g., a phone, a tablet, a custom interface device, or the like) and store data (e.g., raw data from the sensors, the continuous $SpO_2$, and HR/PR estimates).

The wearable device 310 can include attachment mechanism 314. The attachment mechanism 314 can be used to fasten the wearable device 310 on a limb of a neonate such that at least a portion of the at least one photoplethysmography sensor (e.g., part of sensor unit 316) can extend through the housing 312 and can touch the skin of the neonate. The attachment mechanism 314 can be, for example, an elastic band that can be stretched to fit over an appendage of a neonate (e.g., a foot) and then slowly released to constrict to secure the wearable device to the appendage. In other examples, not shown, the attachment mechanism 314 can include a snap, a buckle, an adhesive backing, or any other method of securing the wearable device on the neonate with an appropriate contact pressure so as to not distort the pleth data or the motion data readings. The housing 312 can be rectangular as shown but can be any three-dimensional shape that can enclose the components as discussed above. A hole in the housing 312 through which the sensor unit 316 can be seen can also be any shape that enables the sensor unit 316 to be partially enclosed, but not fully enclosed in the housing. The housing 312 can be made of for example, a plastic or polymer material.

Figure 4:
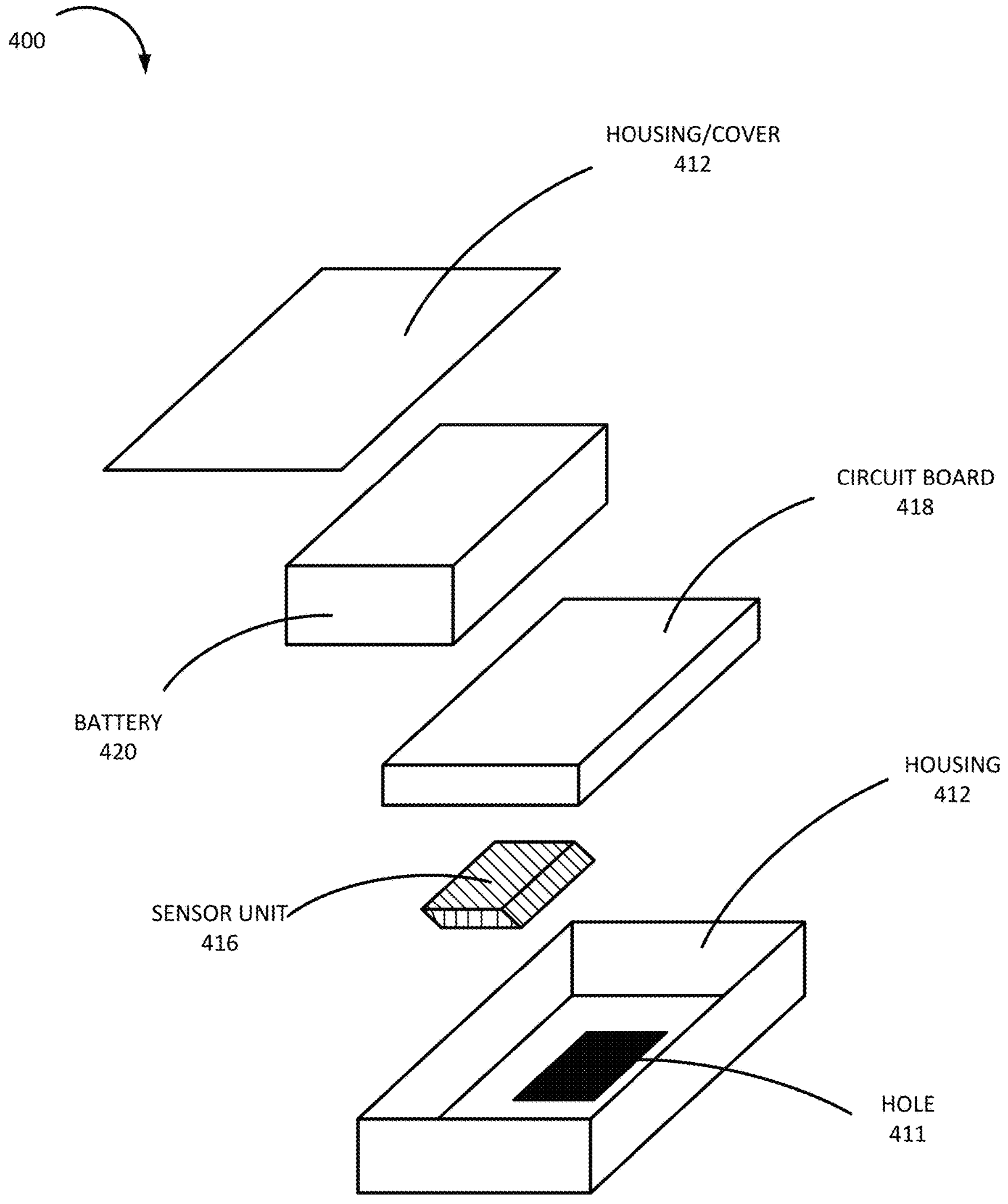
FIG. 4 shows an exploded view of the example wearable device of FIG. 1.

FIG. 4 shows exploded view 400 of the housing of the exemplary wearable device shown in FIG. 3. FIG. 4 shows the body of the housing 412 that includes a hole 411 on the underside (e.g., the side that comes into contact with the skin of the neonate) through which at least a portion of the sensor unit 416 can extend. The sensor unit 416 can include the at least one photoplethysmography sensor, the IMU, and the pressure sensor. A circuit board 418 can be stacked on top of the sensor unit 416 and can include, for example, at least one of the circuits that connects the various components of the wearable device, the wireless communication mechanism, and the processor and/or memory. FIG. 5 shows an example block diagram of an example circuit board 418 and the components connected thereto. Battery 420 can be connected to and stacked on top of circuit board 418. The battery 420 can power the wearable device. In the example shown in FIG. 4 the housing comes in two parts and includes a cover 412, but the housing can be manufactured in any suitable manner.

Figure 6:
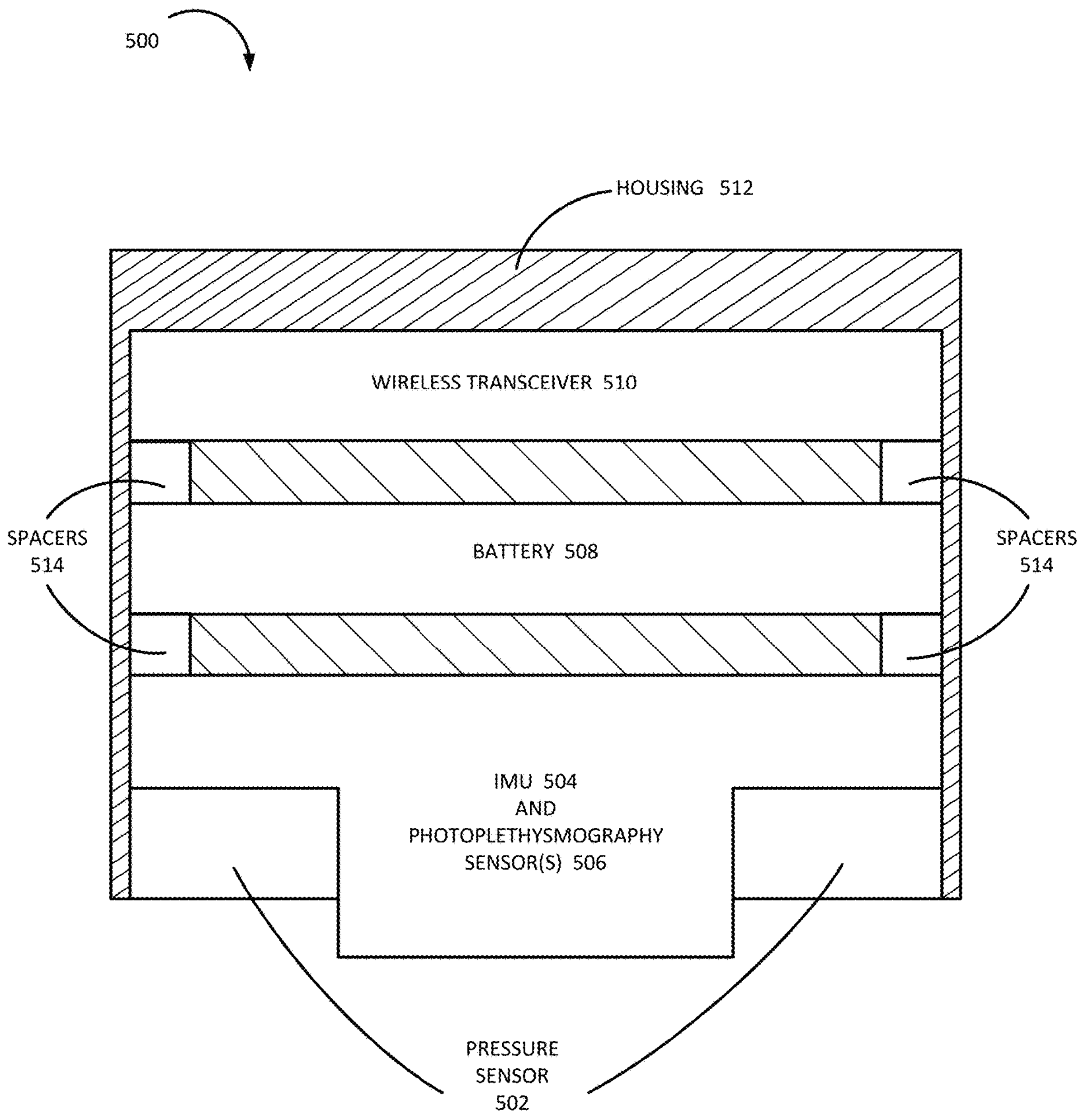
FIG. 6 shows an illustration of a cut view of another example of the wearable device of FIG. 1.

FIG. 6 shows a slice 500 of another example of a wearable device, attachment mechanism not shown, that includes at least one pressure sensor 502. The at least one pressure sensor 502 can be stacked on top of at least a portion of the at least one photoplethysmography sensor 506 and the IMU 504 (e.g., closer to the skin). The at least one pressure sensor 502 can be on a different level from the other portion of the at least one photoplethysmography sensor 506 and IMU 504 as shown or can be level with the other portion (not shown). The at least one pressure sensor 502 can measure pressure data of the at least one photoplethysmography sensor 506 against the neonate's skin (not shown). The pressure data can be contact pressure. The at least one photoplethysmography sensor 506 can be stacked on top of the IMU 504. The battery 508 (e.g., the power source) can be stacked on top of the IMU 504 with a space created therebetween by at least one spacer 514 and a wireless transceiver 510 (e.g., a wireless communication mechanism) can be stacked on top of the battery 508 with a space created therebetween by at least another spacer. The housing 512 can fully enclose at least the wireless transceiver 510 and the battery 508. The housing 512 may enclose a processor as well (not shown). The housing 512 can at least partially enclose the IMU 504, the at least one photoplethysmography sensor 506, and the pressure sensor 502.

The processor, of the wearable device and/or of an external device, can determine a quality of the pleth data, received from the at least one photoplethysmography sensor 506, for the time period as acceptable or unacceptable based on the motion data, received from the IMU 504, for the time period and pressure data, received from the at least one pressure sensor 502 for the time period. The pressure data can be used to determine if the quality of the pleth data is acceptable when the photoplethysmography sensor 506 is in direct contact with the skin of the neonate (or other infant). A photoplethysmography sensor 506 can work at an optimal level when in contact with the skin at a pressure within a preferred range. If the pressure data meets a predefined range of pressure values that indicate the wearable device is mounted correctly on the neonate, then the processor considers the pleth data acceptable. If the pressure data is outside of the range, then the pleth data is determined to be unacceptable. Motion data from the IMU 504 can also be used as part of the data quality analysis. When the processor determines the data quality is acceptable, then the processor can estimate the instantaneous $SpO_2$. When the processor determines the data quality is unacceptable and/or the pressure is too high or too low, then the wearable device 500 can alert a caregiver of the neonate of the problem and how to fix the problem (e.g., a notification can be sent to an external device associated with the caregiver (not shown)). Additionally, the wearable device 500 (or any other aspects of the system 100 described throughout such as the external device 118 in FIG. 1) can make predictions of future oxygen saturation based on trends in the data. For example, the processor can compare the estimated instantaneous $SpO_2$ for the current time period with another $SpO_2$ value for one or more previous time periods, then determine a trend of the estimated instantaneous $SpO_2$ over the one or more previous time periods and the time period, and then generate a warning when the trend of the estimated instantaneous $SpO_2$ is trending towards a watch or dangerous categorization. The warning can be at least one of an audible alarm, a haptic alarm, or a visual change on a display of an external device associated with a caregiver of the neonate.

IV. Methods

Another aspect of the present disclosure can include methods 700-1000 (FIGS. 7-10) for predicting and/or preventing cases of sudden unexpected infant death (SUID) caused by Sudden Unexpected Postnatal Collapse (SUPC) utilizing a combination of pleth data, motion data, and optionally, pressure data to estimate $SpO_2$. Being able to take estimates of instantaneous $SpO_2$ non-invasively is an advantage over traditional invasive and expensive methods of monitoring $SpO_2$. The methods 700-1000 can utilize a system that includes a wearable device (shown in FIGS. 1-6, configured for a neonate and/or an infant) to record data from a neonate (or an infant of any age) and analyze that data to determine the current and/or trending $SpO_2$ of the neonate so preventative or life saving measures can be taken. At least one step of each of the methods can be executed by at least one component, such as the wearable device itself and/or an external device, which may be associated with a caregiver of the neonate, (e.g., mobile device, computer, base station, etc.) that includes at least a processor.

For purposes of simplicity, the method is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method, nor is the method necessarily limited to the illustrated aspects.

Figure 7:
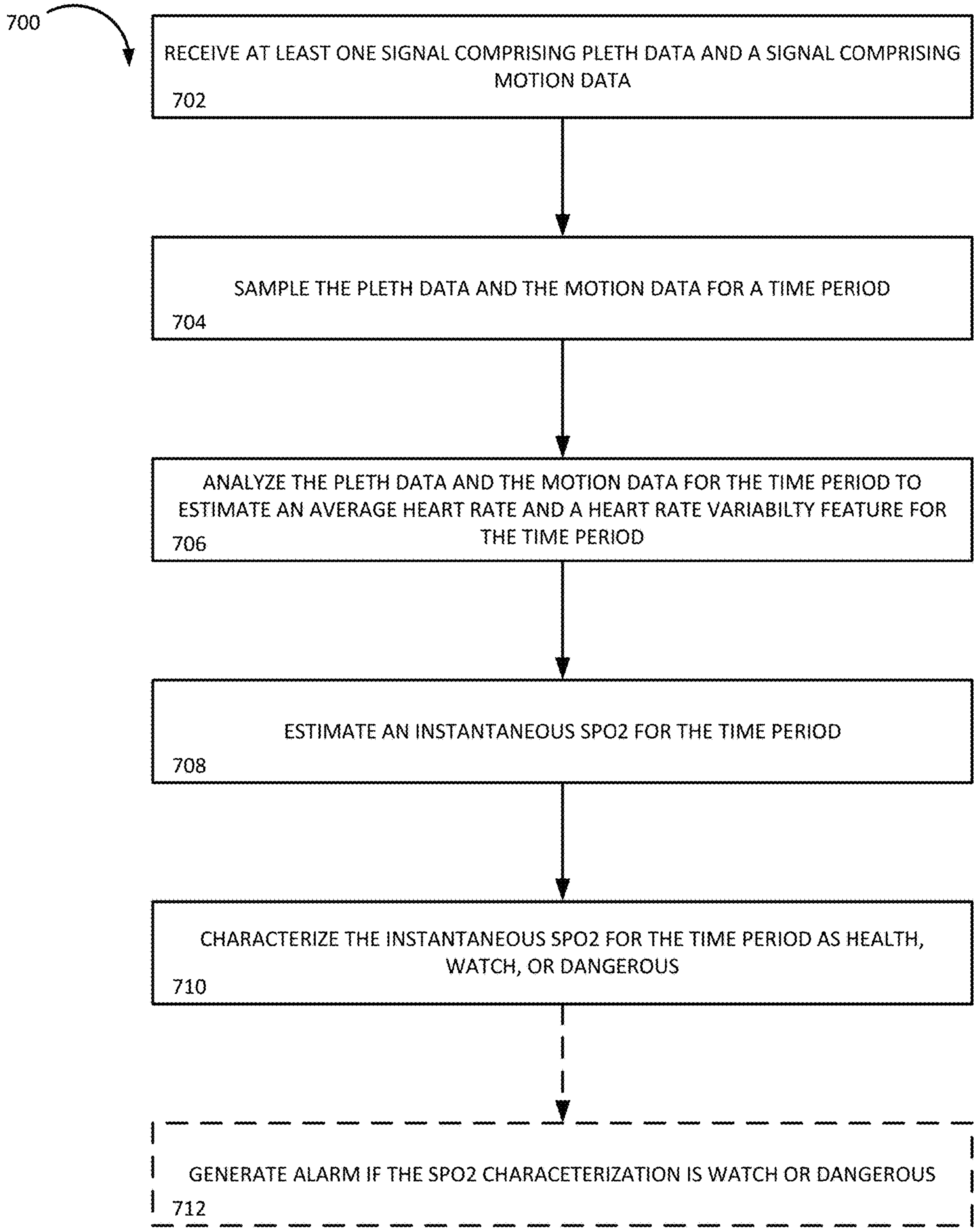
FIGS. 7 and 8 are process flow diagrams illustrating methods for monitoring $SpO_2$ in a neonate (or other infant)

Referring now to FIG. 7, illustrated is a method 700 for preventing SUPC in neonates, or other infants. At step 702, at least one signal that can include pleth data from at least one photoplethysmography sensor (including one or more light sources and a photodetector) of a wearable device can be received by a system comprising a processor. Another signal that can include a motion data signal from an inertial measurement unit (IMU) of the wearable device can also be received by the system. At step 704, the pleth data for a time period (e.g., 5 seconds, 10 seconds, 30 seconds, 1 minute, 5 minutes, 30 minutes, 1 hour, etc.) and the motion data for the same time period can be sampled by the system. The time period can be a preprogrammed time period and/or can be set by a caregiver or medical professional. However, in instances where the time period is set by the caregiver or medical professional, and/or can be determined and/or adjusted dynamically in real-time by the device depending on the current state of the systems, e.g. estimated $SpO_2$ or and/or estimated $SpO_2$ trend. However, in instances where the time period is set by the caregiver or medical professional, there may be a preprogrammed minimum time period and/or maximum time period. At step 706, the pleth data for the time period and the motion data for the time period can be analyzed to estimate an average heartrate and at least one heartrate variability feature for the time period. At step 708, an instantaneous $SpO_2$ of the neonate wearing the wearable device for the time period can be estimated based on the pleth data for the time period and the at least one heartrate variability feature for the time period. At step 710, the instantaneous $SpO_2$ for the time period can be characterized as healthy, watch, or dangerous. For example, a healthy characterization can be given when the instantaneous $SpO_2$ is 95 or above, a watch characterization can be given when the instantaneous $SpO_2$ is between 94 and 89, a dangerous characterization can be given when the instantaneous $SpO_2$ is 88 or below; additionally, the characterization thresholds can be any other values considered medically relevant based on population data or can be set by a health professional and/or caregiver (within predetermined safety limits). Additionally, and/or alternatively (but not shown) the instantaneous $SpO_2$ can be compared with previous $SpO_2$ values and used to predict future $SpO_2$ of the neonate based on trends in the $SpO_2$ over different time periods. At step 712, in some instances, an alarm can be generated when the instantaneous $SpO_2$ (and/or the predicted future $SpO_2$) is characterized as watch or dangerous indicating an enhanced risk of SUPC. The alarm can be at least one of audio, haptic, and visual. The alarm can emit from the wearable device and/or from the external device (e.g., a mobile phone, a computer, a base station, etc.) associated with the caregiver and/or health professional. In other instances, the pleth data can be visualized, without an alarm, on a display associated with an external device for a caregiver and/or health professional to review while the wearable device is active.

Figure 8:
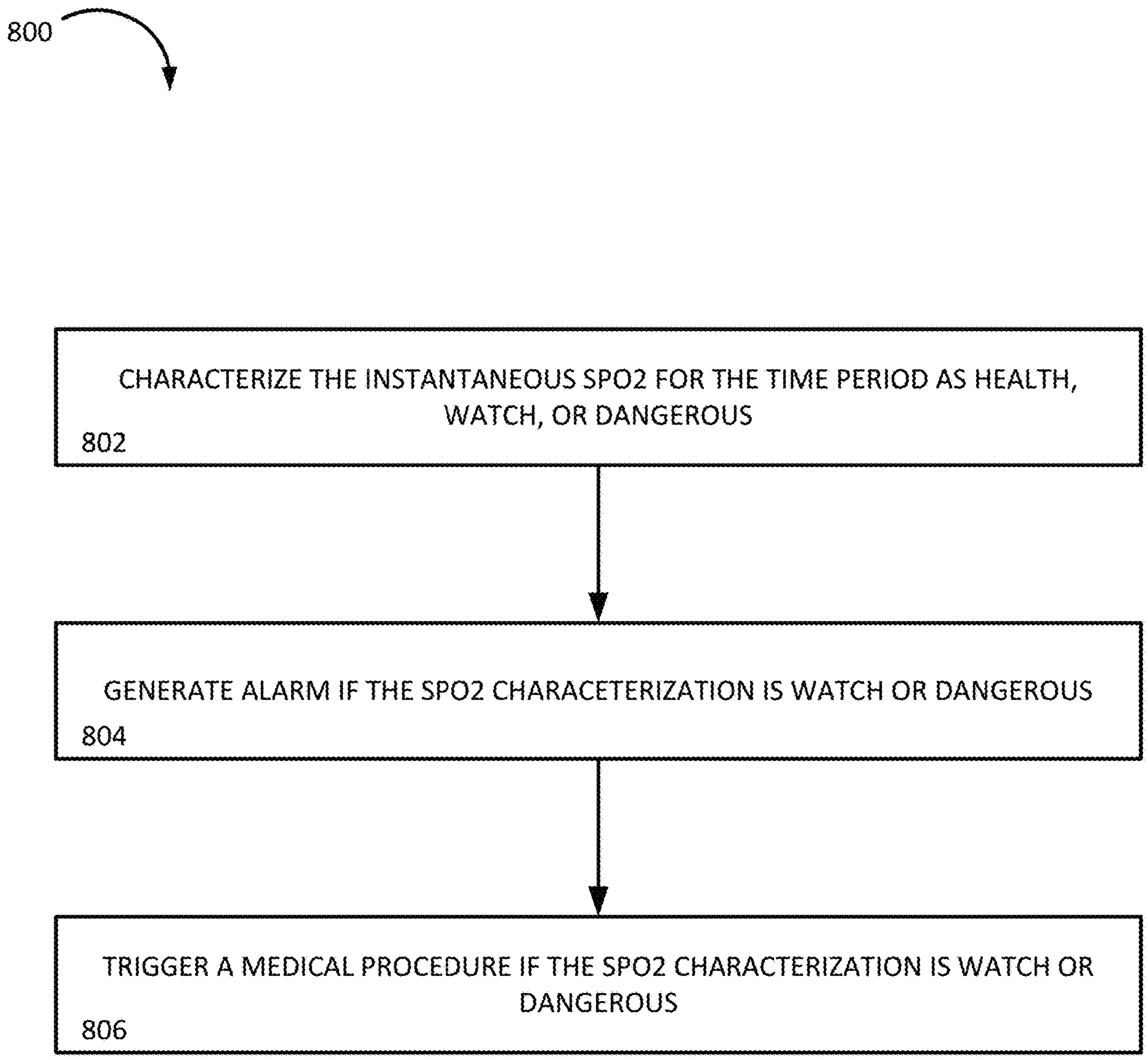

Referring now to FIG. 8, illustrated is a method 800 for providing a preventative and/or life-saving treatment for a neonate. At step 802, the system can characterize the instantaneous $SpO_2$ of the neonate for a given time period as healthy (e.g., 95 or above), watch (e.g., 94 and 89), or dangerous (e.g., 88 or below). At step 804 the system can alarm if the instantaneous $SpO_2$ is characterized as watch or dangerous. At step 806, the system can trigger a medical device in communication with the wearable device to execute a medical procedure on the neonate when the instantaneous $SpO_2$ is characterized as watch or dangerous. For example, the medical device can include an oxygen source and a cannula (or other delivery device), and the medical procedure can include delivery of supplemental oxygen to the neonate. In another example, the medical device can include a tactile stimulator and the medical procedure can include tactile stimulation of the neonate.

Figure 9:
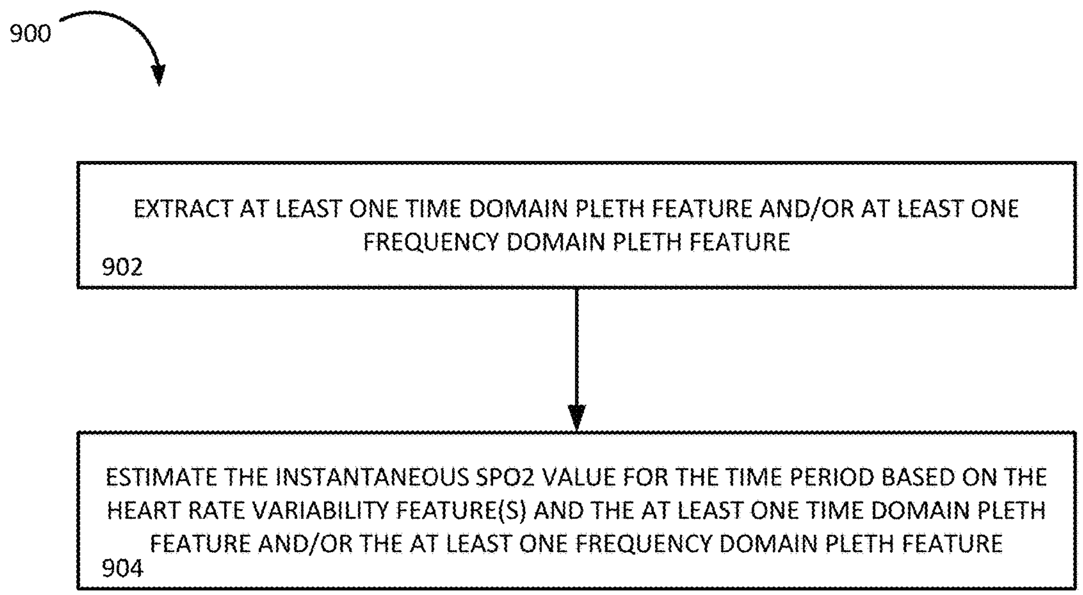
FIG. 9 is a process flow diagram illustrating a method for analyzing pleth and motion data.

Referring now to FIG. 9, illustrated is a method 900 for analyzing the pleth data and the motion data as part of preventing SU PC. At 902, the system can extract at least one time-domain pleth feature and/or extract at least one frequency-domain pleth feature from the pleth data. For example, at least a portion of the pleth data can be converted from the time-domain to the frequency-domain (or vice versa) via a Fourier Transform, a Z transform, a Laplace Transform, or the like. At step 904, the system can estimate the instantaneous $SpO_2$ value for the time period based on the at least one heartrate variability features for the time period and the at least one time-domain pleth feature and/or the at least one frequency-domain pleth feature. The estimation can be part of the characterization analysis. Additionally, the system can compare the estimated instantaneous $SpO_2$ value for the time period with another instantaneous $SpO_2$ value for one or more previous time periods and determine a trend of the estimated instantaneous $SpO_2$ of the neonate. The trends can be determined, for example, for the previous 5 minutes, 10 minutes, hour, day, or the like and/or can include lifestyle schedule information (e.g., feeding times, nap times, changing times, etc.). The system can generate one or more warnings (e.g., audio, visual, and/haptic) when the trend of the estimated instantaneous $SpO_2$ is trending towards a watch or dangerous categorization. Different warnings can be generated for trend towards watch or dangerous. The system may also be able to trigger a medical device and/or call medical professionals and/or emergency services.

Figure 10:
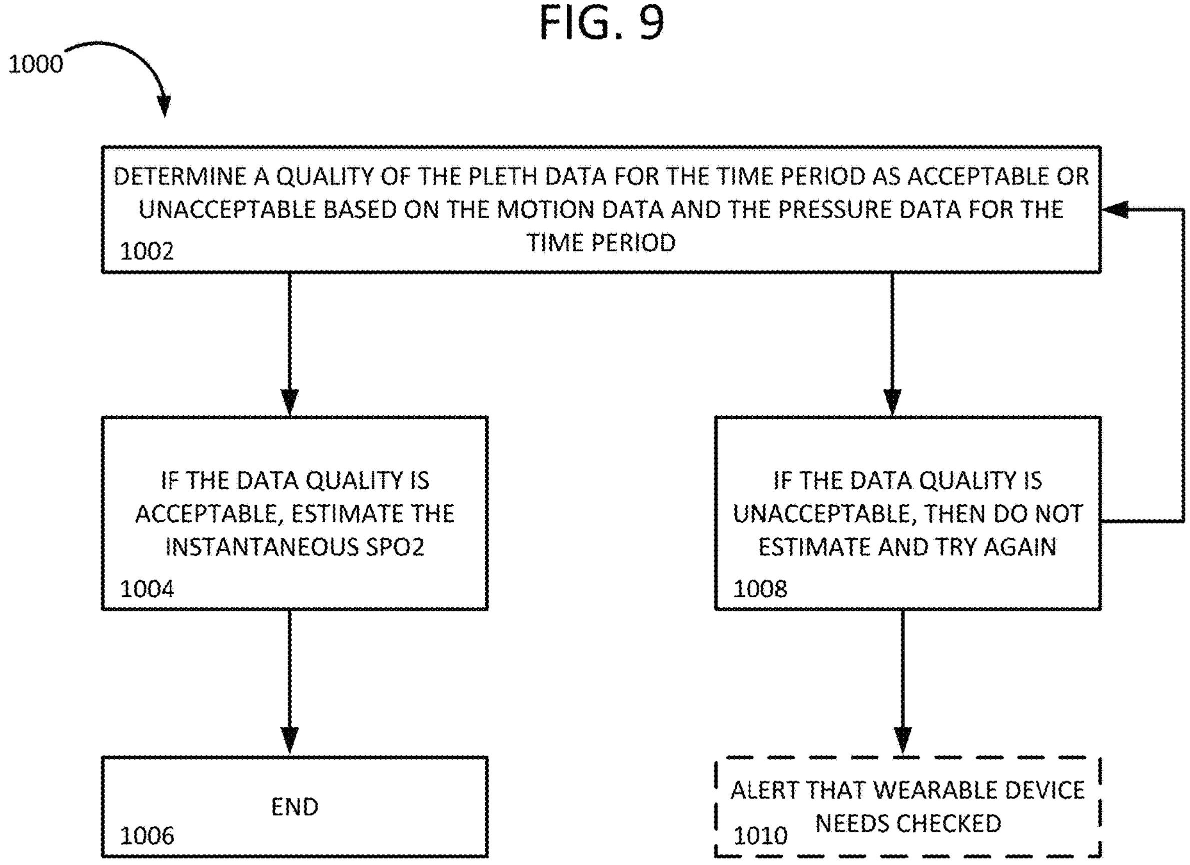
FIG. 10 is a process flow diagram illustrating a method for determining data quality of the pleth data.

Referring now to FIG. 10, illustrated is a method 1000 for determining the data quality of the wearable device. Data quality can be determined to reduce the number of false alarms (increase Specificity) while simultaneously increasing the detection of low $SpO_2$ (increased Sensitivity). At step 1002, the system can determine a quality metric of the pleth data for the time period as acceptable or unacceptable. The acceptable or unacceptable decision can be based on the motion data for the time period and pressure data for the time period. The motion data and pressure data can be compared with known ranges of acceptable and unacceptable motion and pressure data. For example, pressure data can be considered unacceptable if the pressure data indicates the wearable device is too loose (below a low range of acceptable pressure) or too tight (above a high range of acceptable pressure) and/or the motion data can be considered unacceptable if, in one instance, the device has too much linear or rotational motion (e.g., is too loose so that the device may not contact the skin correctly at all times). As an example, the pressure data can be received from a pressure sensor built into the skin surface side of the wearable device. The pressure data can be the pressure of the contact between the skin of the neonate and at least a portion of the wearable device and/or the at least one photoplethysmography sensor of the wearable device. At step 1004, if the data quality is acceptable, then the system can estimate the instantaneous $SpO_2$. At step 1006, the quality determination ends because the data quality is acceptable. At step 1008, if the data quality is unacceptable, then the system cannot estimate the instantaneous $SpO_2$ and can determine the data quality again for one or more time period (e.g., a preset number or a number set by a caregiver, such as 1, 2, or 5 time periods) and/or, at step 1010, the system can alert a caregiver and/or medical professional that the wearable device needs to be checked (e.g., has come off the neonate, is not properly fastened on the neonate, or has another defect). The alert can be at least one of audible, tactile, and visual. For example, the alert can appear as a notification on a mobile device, computer, or base station.

V. Example Use

In this example use, a wearable device, as described above, is used to monitor an estimated instantaneous oxygen saturation ($SpO_2$) in a neonate to predict and prevent cases of Sudden Unexpected Infant Death (SUID) caused by Sudden Unexpected Postnatal Collapse (SUPC).

The wearable device, embodied in a small package, was placed on a foot (in this example, the left foot, but it should be understood that the wearable device can alternatively be placed on the right foot) of a neonate and secured to the foot with a bandage type wrap around the foot and ankle. A plethysmography sensor faced the skin of the bottom of the foot (also referred to as the sole of the foot) to provide pleth waveforms based on four wavelength ranges (infrared, red, green, and blue) with unique and complimentary estimations for estimating instantaneous $SpO_2$. One or more pressure sensors detected whether the wearable device correctly contacted the bottom of the left foot (e.g., with the proper amount of pressure), and were linked with a display device (LED(s), screen, etc.) to display a warning light or notification if the contact was improper. Additionally, at least one inertial measurement unit (IMU) was continuously detecting motion data such as linear and angular accelerations, linear and angular velocities, orientation, and the like. The motion data was used with the pleth data and/or the pressure data for computations and estimations of $SpO_2$.

The instantaneous $SpO_2$ in the neonate was estimated by:

a. Four LEDs (an infrared (IR) LED, a red (A) LED, a green (G) LED, and a blue (B) LED) of the plethysmography sensor were turned on and off in a sequence with the duty cycle and power for each LED controlled by the wearable device according to a pre-programmed sequence). The photodetector of the plethysmography sensor then collected the reflected light from each of the LEDs (reflected off the skin of the neonate's foot) at a sample rate, which was controlled by the wearable device. The photodetector converted the reflected light into pleth waveforms (one for each of the IR, R, G, and B reflections) and stored the IR, R, G, and B pleth waveforms over a time period. The time period was programmed, and could be changed, by an external device.

b. The IR, R, G, and B pleth waveforms were then analyzed in the time-domain and the frequency domain and features in both domains were extracted from each pleth waveform. Typical features extracted from the pleth waveforms include heart rate/pulse rate (HR/PR), non-pulsatile (DC) and pulsatile (AC) components of blood flow, and measures of pulse rate (PR) variability.

c. An estimate of $SpO_2$ at the time was then determined by analyzing the features extracted from the pleth waveform data. A new estimate of instantaneous $SpO_2$ was obtained every 1-second and compared against previous estimates. A sliding window approach allowed reevaluation of the estimates of $SpO_2$ every one minute.

d. The accuracy of the $SpO_2$ estimates were conditioned on the analysis of raw motion data from the IMU and raw pressure data from the pressure sensor that ensured the sensor maintained good contact with the sole of the foot. If either predetermined motion and pressure criteria for good signal quality were not satisfied, the $SpO_2$ estimate was not updated from the previous value, the sliding window was incremented, and the new data was analyzed. Additionally, if motion and pressure criteria were not met for a predetermined amount of time, then alerts were generated to indicate lack of motion, too much motion, and improper contact pressure between the wearable device and the neonate's skin.

e. Predictions of future values of $SpO_2$ estimates were determined using at least an analysis of HR/PR variability compared to clinically predetermined thresholds to predict if oxygen saturation was moving towards a cautionary or unsafe range. In this example, an alert was generated when the instantaneous $SpO_2$ was less than 92 and a warning was generated when the instantaneous $SpO_2$ was trending in the direction of 92.

With the estimate of the instantaneous $SpO_2$ and the predictions of future trends in $SpO_2$, a caregiver can know when the neonate is experiencing or is on track to experience SUPC.

From the above description, those skilled in the art will perceive improvements, changes, and modifications. Such improvements, changes and modifications are within the skill of one in the art and are intended to be covered by the appended claims.

The following is claimed:

1. A wearable device configured to be worn by a neonate or infant, the wearable device comprising:
   a housing comprising a sensor unit, wherein the sensor unit comprises:
      at least one photoplethysmography sensor configured to be placed against the neonate's skin and to measure pleth data; and
      an inertial measurement unit (IMU) configured to collect motion data of the neonate,
      wherein at least a portion of the at least one photoplethysmography sensor and the IMU are configured to be at least partially enclosed by the housing; and
   an attachment mechanism configured to fasten at least a portion of the housing comprising the at least one photoplethysmography sensor to the neonate's skin,
   wherein the at least one photoplethysmography sensor and the IMU are in communication with a processor that:
      samples the pleth data for a time period and the motion data for the time period;
      analyzes the pleth data for the time period and the motion data for the time period to estimate an average heartrate and compute at least one heartrate variability features for the time period;
      estimates an instantaneous $SpO_2$ for the time period based on the pleth data for the time period, the motion data for the time period, and the at least one heartrate variability features for the time period;
      characterizes the instantaneous $SpO_2$ as healthy, watch, or dangerous for Sudden Unexpected Postnatal Collapse;
      issues an alert when the instantaneous $SpO_2$ is characterized as watch or dangerous for Sudden Unexpected Postnatal Collapse; and
      triggers a medical device in communication with the wearable device to perform a medical procedure on the neonate when the instantaneous $SpO_2$ is characterized as watch or dangerous, wherein the medical procedure comprises a mechanical tactile stimulation and/or application of supplemental oxygen.

2. The wearable device of claim 1, wherein the processor analyzes the pleth data for the time period by extracting at least one time-domain pleth feature and/or extracting at least one frequency-domain pleth feature.

3. The wearable device of claim 2, wherein an instantaneous $SpO_2$ value for the time period is estimated based on the heartrate variability features for the time period and the at least one time-domain pleth feature and/or the at least one frequency-domain pleth feature.

4. The wearable device of claim 1, further comprising at least one pressure sensor stacked on top of at least a portion of the at least one photoplethysmography sensor and configured to measure pressure data of the at least one photoplethysmography sensor against the neonate's skin, wherein the at least one photoplethysmography sensor is stacked on top of the IMU.

5. The wearable device of claim 4, wherein the processor determines a quality of the pleth data for the time period as acceptable or unacceptable based on the motion data for the time period and/or pressure data for the time period.

6. The wearable device of claim 5, wherein the processor estimates the instantaneous $SpO_2$ when the data quality is acceptable.

7. The wearable device of claim 1, wherein the processor:
   compares the estimated instantaneous $SpO_2$ for the time period to another $SpO_2$ value for one or more previous time periods;
   determines a trend of the estimated instantaneous $SpO_2$; and
   generates a warning when the trend of the estimated instantaneous $SpO_2$ is trending towards a watch or dangerous categorization.

8. The wearable device of claim 1, wherein the at least one photoplethysmography sensor comprises at least one of: an infrared (IR) light source, a red light source, a blue light source, or a green light source.

9. The wearable device of claim 1, further comprising a wireless communication mechanism, wherein the wireless communication mechanism is configured to transmit the pleth data and the motion data to a base station according to a wireless communication protocol.

10. The wearable device of claim 9, wherein the wireless communication protocol is BLUETOOTH low energy.

11. The wearable device of claim 1, further comprising a power source and a wireless communication mechanism fully enclosed in the housing.

12. The wearable device of claim 1, wherein at least a portion of the at least one photoplethysmography sensor extends through the housing and is configured to touch the skin of the neonate.

13. A method for preventing Sudden Unexpected Postnatal Collapse, the method comprising:
   receiving, by a system comprising a processor, at least one signal comprising pleth data from at least one photoplethysmography sensor of a wearable device and a signal comprising motion data signal from an inertial measurement unit (IMU) of the wearable device, wherein the at least one photoplethysmography sensor and the IMU are co-located at least partially within a housing of the wearable device;
   sampling, by the system, the pleth data for a time period and the motion data for the time period;
   analyzing, by the system, the pleth data for the time period and the motion data for the time period to estimate an average heartrate and at least one heartrate variability feature for the time period;
   estimating, by the system, an instantaneous $SpO_2$ of a neonate wearing the wearable device for the time period based on the pleth data for the time period and the at least one heartrate variability feature for the time period; and
   characterizing, by the system, the instantaneous $SpO_2$ for the time period as healthy, watch, or dangerous for Sudden Unexpected Postnatal Collapse,
   wherein when the instantaneous $SpO_2$ is characterized as watch or dangerous:
      issuing, by the system, an alarm indicating an enhanced risk of Sudden Unexpected Postnatal Collapse, and
      triggering, by the system, a medical device in communication with the wearable device to perform a medical procedure on the neonate, wherein the medical procedure comprises a mechanical tactile stimulation and/or application of supplemental oxygen.

14. The method of claim 13, wherein the analyzing further comprises extracting at least one time-domain pleth feature and/or extracting at least one frequency-domain pleth feature.

15. The method of claim 14, wherein the instantaneous $SpO_2$ value for the time period is estimated based on the at least one heartrate variability features for the time period and the at least one time-domain pleth feature and/or the at least one frequency-domain pleth feature.

16. The method of claim 13, further comprising determining a quality of the pleth data for the time period as acceptable or unacceptable based on the motion data for the time period and/or pressure data for the time period.

17. The method of claim 16, wherein the instantaneous $SpO_2$ is estimated when the data quality is acceptable.

* * * * *